(12) United States Patent
Fifolt et al.

(10) Patent No.: US 9,498,605 B2
(45) Date of Patent: Nov. 22, 2016

(54) EXTERNAL VOLUME-LIMITING CSF DRAINAGE SYSTEM

(71) Applicant: DEPUY SYNTHES PRODUCTS, INC., Raynham, MA (US)

(72) Inventors: Douglas Fifolt, Wrentham, MA (US); Carl Turgeon, Pocassett, MA (US); Thomas Boden, Jr., Willowtree Lane, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 317 days.

(21) Appl. No.: 14/230,578

(22) Filed: Mar. 31, 2014

(65) Prior Publication Data

US 2015/0273192 A1 Oct. 1, 2015

(51) Int. Cl.
*A61M 5/00* (2006.01)
*A61M 27/00* (2006.01)

(52) U.S. Cl.
CPC ........... *A61M 27/006* (2013.01); *A61M 27/00* (2013.01)

(58) Field of Classification Search
CPC ............. A61M 27/006; A61M 27/00; A61M 27/002; A61M 5/14276; A61M 2002/0464; A61M 2210/0693; A61M 2005/8287; A61M 2027/004; A61M 1/0019; A61M 1/0021; A61M 1/0023; A61M 1/0049; A61M 1/005
USPC .............. 604/8–10, 317–319, 415, 540–544
See application file for complete search history.

(56) References Cited

U.S. PATENT DOCUMENTS

| | | | |
|---|---|---|---|
| 4,026,298 A | 5/1977 | Grausz | |
| 4,500,311 A | 2/1985 | Redmond | |
| 4,540,400 A | 9/1985 | Hooven | |
| 4,551,128 A * | 11/1985 | Hakim | A61M 27/006 137/508 |
| 5,207,661 A | 5/1993 | Repschlager | |
| 5,683,357 A * | 11/1997 | Magram | A61M 1/0021 604/8 |
| 5,772,607 A | 6/1998 | Magram | |
| 8,221,366 B2 | 7/2012 | Hoffman | |
| 8,322,365 B2 | 12/2012 | Wilson | |
| 8,460,256 B2 * | 6/2013 | Michaels | A47L 5/365 137/565.23 |
| 9,295,821 B2 * | 3/2016 | Miethke | A61M 27/006 |
| 2009/0054857 A1 | 2/2009 | Eckermann | |
| 2012/0283676 A1 | 11/2012 | Hoffman | |

FOREIGN PATENT DOCUMENTS

EP 688189 B2 12/1995
EP 798011 A1 10/1997

* cited by examiner

*Primary Examiner* — Philip R Wiest

(57) ABSTRACT

A system and method for draining at least one type of bodily fluid from a patient, including a chamber capable of being adjusted to hold one of at least a first volume of fluid and a second, smaller volume of fluid. The chamber has an inlet end with a barrier defining an opening and has an outlet end defining an outlet passage. The system further includes a valve with a valve seat and a valve closure member to define a usable volume within the chamber, and a movable adjustment member with a shaft passable through the opening in the barrier and terminating within the chamber at a first end. The first end of the shaft is connected to the valve seat, and the shaft has a plurality of features along its length engagable with corresponding engagement features in a fixed relationship with the barrier to enable the shaft to be advanced into the chamber to reduce the usable volume to be less than the first volume.

20 Claims, 4 Drawing Sheets

EXTERNAL VOLUME-LIMITING CSF DRAINAGE SYSTEM

BACKGROUND OF THE INVENTION

1. Field of the Invention

The invention relates to techniques and tools to control drainage of bodily fluid from a patient and more particularly to external volume-limiting devices for withdrawing cerebrospinal fluid.

2. Description of the Related Art

There are a number of treatments for medical conditions which require fluid to be removed from an organ or tissue of a patient. One such condition is hydrocephalus, where cerebrospinal fluid abnormally accumulates in the skull faster than it is withdrawn by the body. The excessive build-up of cerebrospinal fluid compresses brain tissues, which eventually leads to brain damage.

Hydrocephalus is commonly treated by implanting a shunt in fluid communication with a ventricle within the brain to withdraw cerebrospinal fluid at a desired rate. Typically, the rate of withdrawal of cerebrospinal fluid, also referred to herein as "CSF", is controlled by a valve having different pressure settings which a clinician adjusts pre-operatively. A number of shunt valves can be noninvasively changed after implantation, such as the Codman® Hakim® programmable valve which is currently commercially available from Codman & Shurtleff, Inc. of Raynham, Mass. Also available from Codman & Shurtleff, Inc. is the CERTAS™ programmable valve that is disclosed and claimed in U.S. Pat. No. 8,322,365 by Wilson et al.

External CSF drainage systems are typically utilized in a clinical setting when it is desirable to drain CSF through a catheter into an external "closed" collection system to prevent infection of the CSF during management of intracranial pressure. Removal of too much CSF, or "over-drainage", through the catheter is undesirable and may result in severe headaches or collapse of one or more ventricular cavities within the brain. To reduce the risk of over-drainage, physicians typically drain CSF at a rate of 10 ml to 50 ml per hour.

Withdrawal of excessive CSF can also result in "over-filling" of the external drainage system. Various problems may result from over-filling, including leakage of fluid from the system and resulting infection through the pathway provided by the leaking fluid.

Many conventional drainage systems crudely control flow rate of CSF by adjusting the level at the which the system is positioned above the head or spine of the patient. In other words, gravity and fluid pressure generated within the patient and within the system affect flow rate into a collection chamber. Flow may unexpectedly increase if the level of the system is lowered in relation to the level of the catheter entering the patient, such as when a patient sits up after lying in a prone position.

One system disclosed by Eckermann in U.S. Patent Publication No. 2009/0054857 attempts to measure the volume of fluid in a collection chamber utilizing one or more sensors. In other words, proper functioning of this system appears to require correct operation of the sensors.

Another system disclosed by Hoffman et al. in U.S. Pat. No. 8,221,366 utilizes a buoyant float to seal an inflow port or a vent port of a chamber. However, this system is not optimal because the volume of the chamber appears to be fixed. Thus, the float does not appear to be adjustable to accommodate different volumes of CSF fluid if a physician selects an alternate volume of CSF to be drained.

It is therefore desirable to have a simple yet reliable and adjustable system and technique to drain bodily fluids such as cerebrospinal fluid.

SUMMARY OF THE INVENTION

An object of the present invention is to provide a system and technique to selectively drain a desired quantity of bodily fluid such as cerebrospinal fluid from a patient.

Another object of the present invention is to provide such a system and technique which easily yet reliably enables adjustment of the volume of bodily fluid actually drained from the patient.

This invention features a system suitable for draining at least one type of bodily fluid, such as cerebrospinal fluid, from a patient. The system includes a chamber capable of being adjusted to hold one of at least a first volume of fluid and a second, smaller volume of fluid. The chamber has an inlet end with a barrier defining an opening and has an outlet end defining an outlet passage. The system further includes a valve with a valve seat and a valve closure member to define a usable volume within the chamber, and a movable adjustment member with a shaft passable through the opening in the barrier and terminating within the chamber at a first end. The first end of the shaft is connected to the valve seat, and the shaft has a plurality of features along at least a portion of its length engagable with corresponding engagement features in a fixed relationship with the barrier to enable the shaft to be advanced into the chamber to reduce the usable volume to be less than the first volume.

In certain embodiments, the valve closure member includes a feature which is buoyant relative to the fluid to be drained, and the valve includes a cage structure to control movement of the buoyant feature between at least first and second positions representing the first volume and the second volume, respectively. In some embodiments, the shaft is rotatable and defines a helical thread along at least a portion of its length. The adjustment member includes a grip member attached to the shaft, the grip member being graspable by a user of the system to impart rotation to the shaft.

In a number of embodiments, the system further includes tubing defining a lumen in fluid communication with the valve seat. Preferably, the shaft defines a longitudinal channel and a portion of the tubing passes through the channel. In some embodiments, a sleeve surrounds at least a portion of the shaft to assist in isolating the shaft from fluid within the chamber, and the barrier includes a filter to restrict entry of microbes past the barrier and into the chamber.

This invention also features a method of adjusting drainage of at least one type of bodily fluid from a patient, including selecting an assembly having a chamber capable of holding one of at least a first volume of fluid and a second, smaller volume of fluid, the chamber having an inlet end with a barrier defining an opening and having an outlet end defining an outlet passage, the assembly further including a valve with a valve seat and a valve closure member to define a usable volume, and a movable adjustment member having a shaft passable through the opening in the barrier and terminating within the chamber at a first end, the first end of the shaft being connected to the valve seat, the shaft having a plurality of features along at least a portion of its length engagable with corresponding engagement features being in a fixed relationship with the barrier to enable the shaft to be advanced into the chamber to reduce the usable volume to be less than the first volume. The method further includes coupling a distal end of a tubing to a medical device in fluid communication with the bodily fluid to be drained, a proximal end of the tubing being in fluid communication with the chamber, and moving the shaft to adjust the usable volume within the chamber.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a system and method for draining at least one type of bodily fluid, such as cerebrospinal fluid, from a patient. The fluid may include fragments of bone, soft tissue, or other debris. The system includes an assembly having a chamber capable of being adjusted to hold one of at least a first volume of fluid and a second, smaller volume of fluid. The chamber has an inlet end with a barrier defining an opening and has an outlet end defining an outlet passage. The system further includes a valve with a valve seat and a valve closure member to define a usable volume within the chamber, and a movable adjustment member with a shaft passable through the opening in the barrier and terminating within the chamber at a first end. The first end of the shaft is connected to the valve seat, and the shaft has a plurality of features along at least a portion of its length engagable with corresponding engagement features in a fixed relationship with the barrier to enable the shaft to be advanced into the chamber to reduce the usable volume to be less than the first volume.

Figure 1:
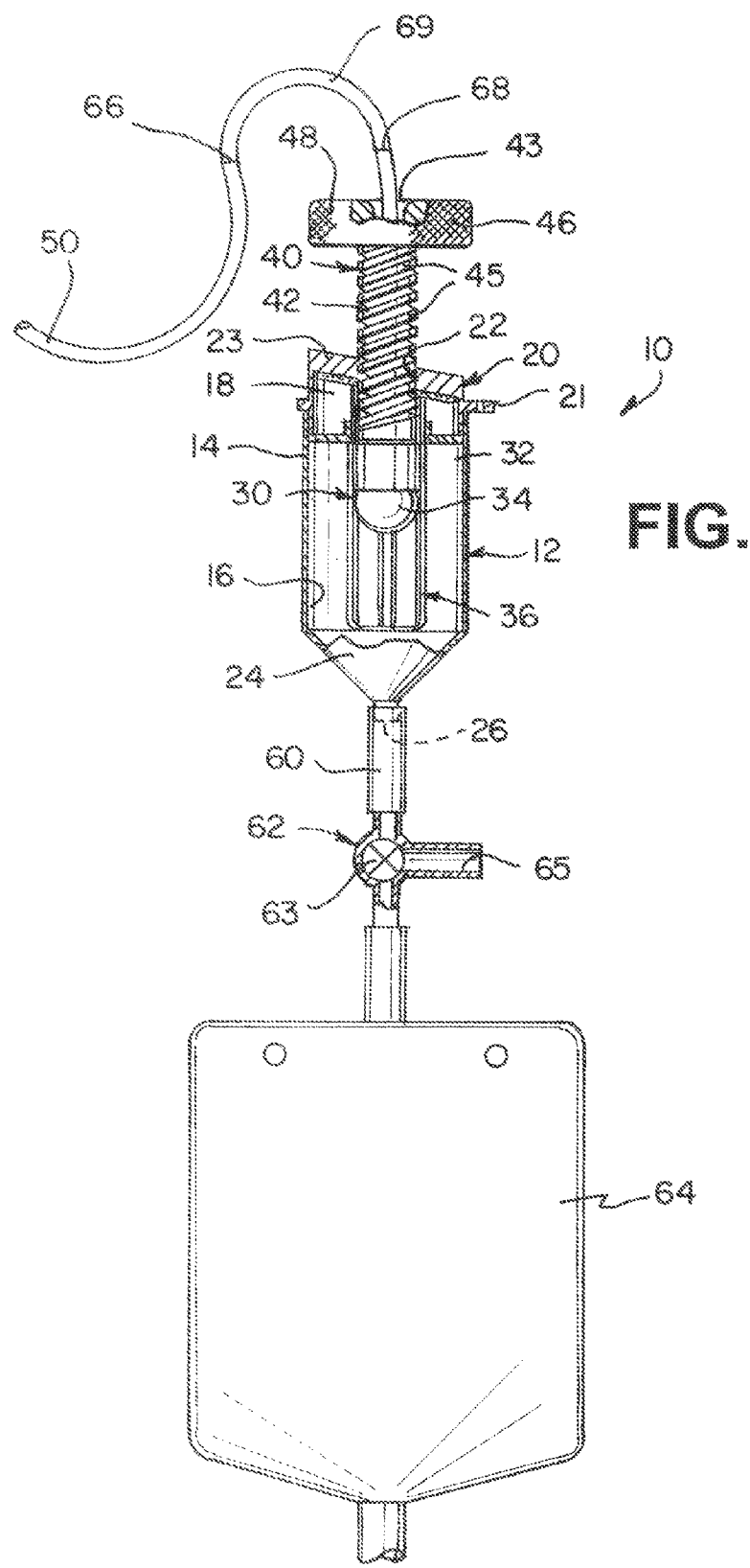
FIG. 1 is a schematic, partial cross-sectional view of an external drainage system according to the present invention connected to a secondary drainage bag via a secondary drain valve with sampling port.

System 10 according to the present invention, FIG. 1, includes an assembly 12 having a housing 14 that defines a volume-limiting containment chamber 16 capable of being adjusted to hold one of at least a first volume of fluid and a second, smaller volume of fluid. The chamber 16 has an inlet end 18 with a barrier 20, such a cap with rib 21 and a cover 23 defining an opening 22, the barrier 20 being fixed to housing 14 in one construction and, in another construction, being removably attached. Chamber 16 also has an outlet end 24 defining an outlet passage 26.

Figure 2:
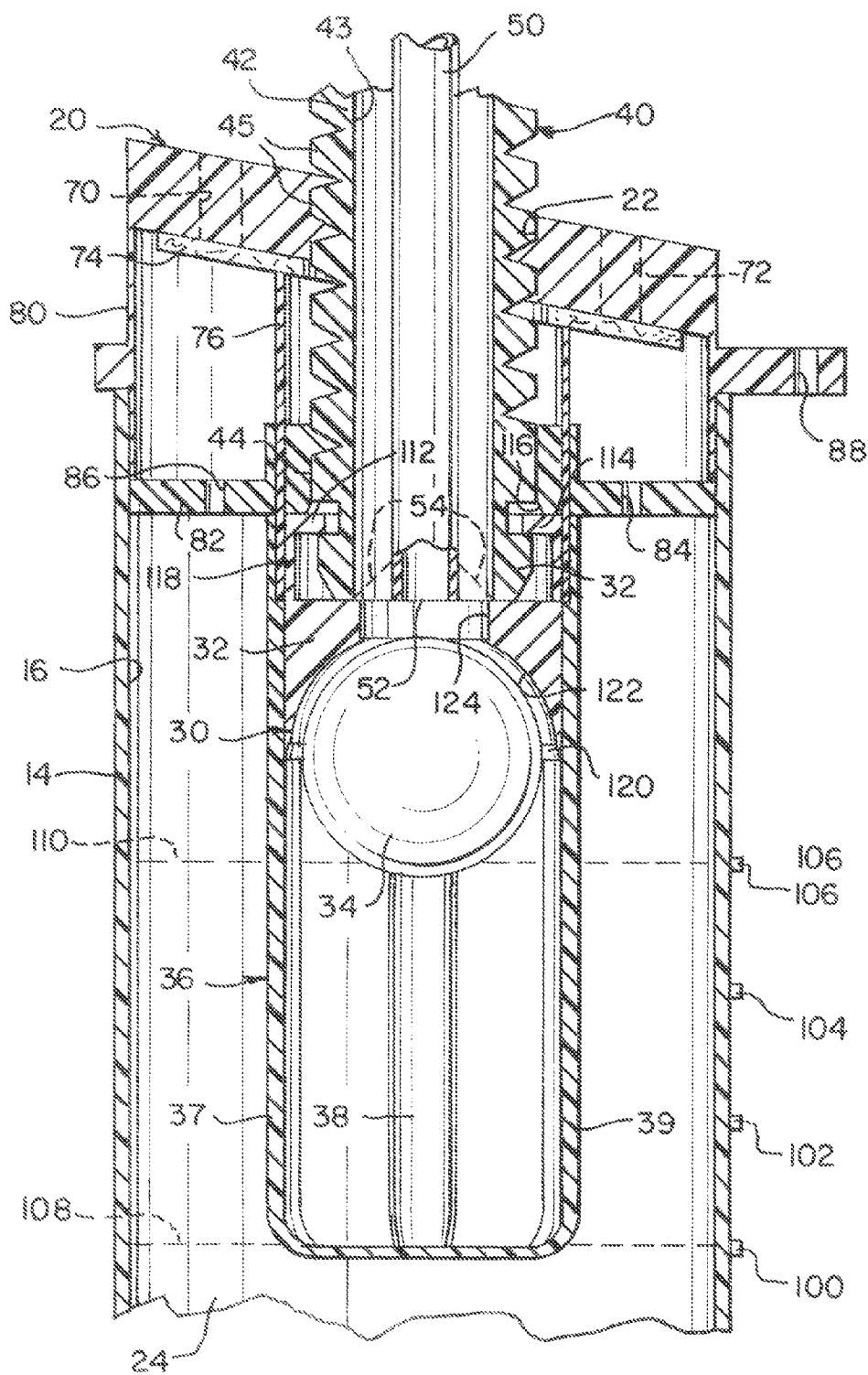
FIG. 2 is an enlarged partial side cross-sectional view of the drainage system of FIG. 1.
Figure 3:
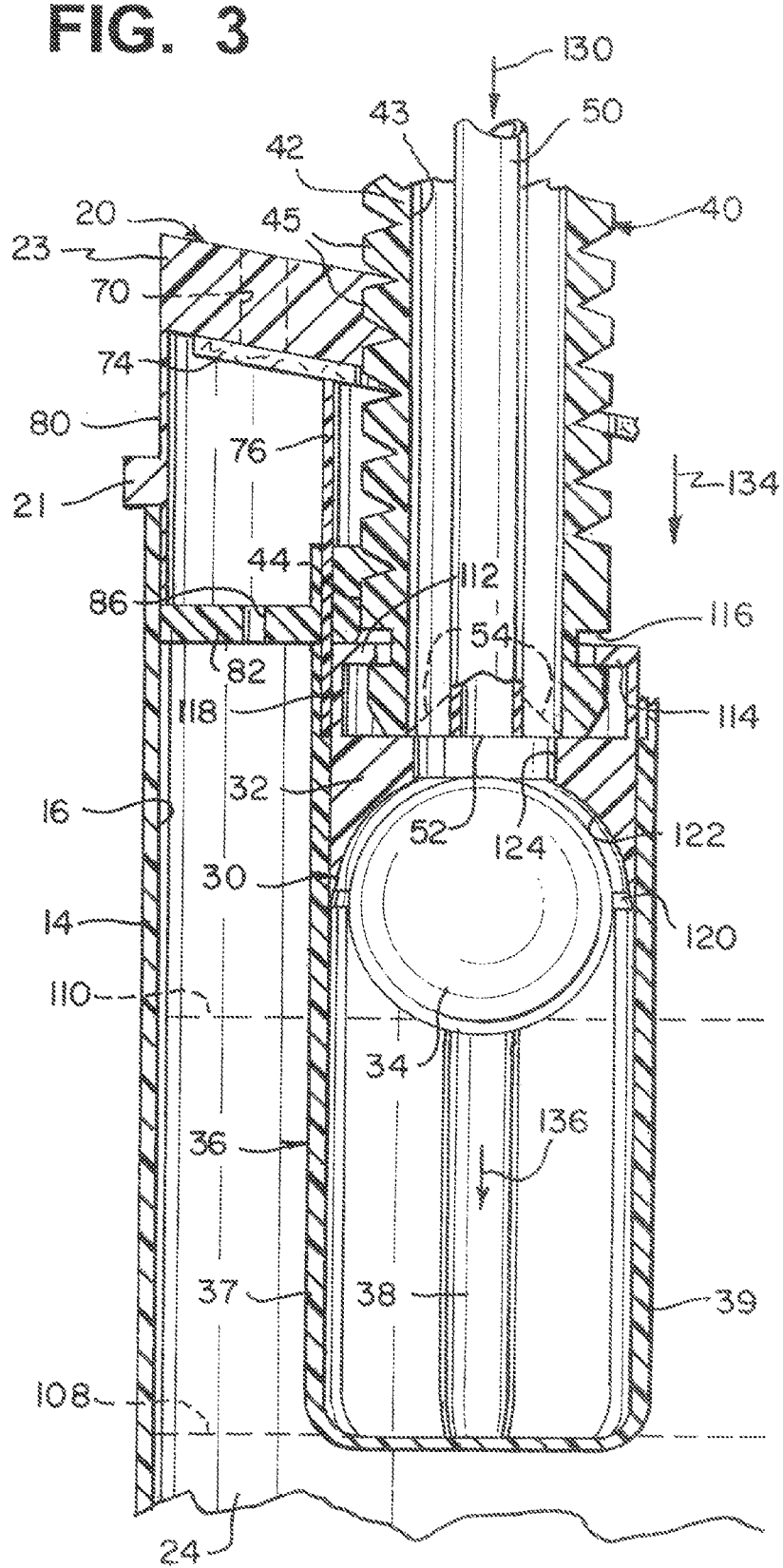
FIG. 3 is a view of the drainage system of FIG. 2 with some components removed for clarity.
Figure 4:
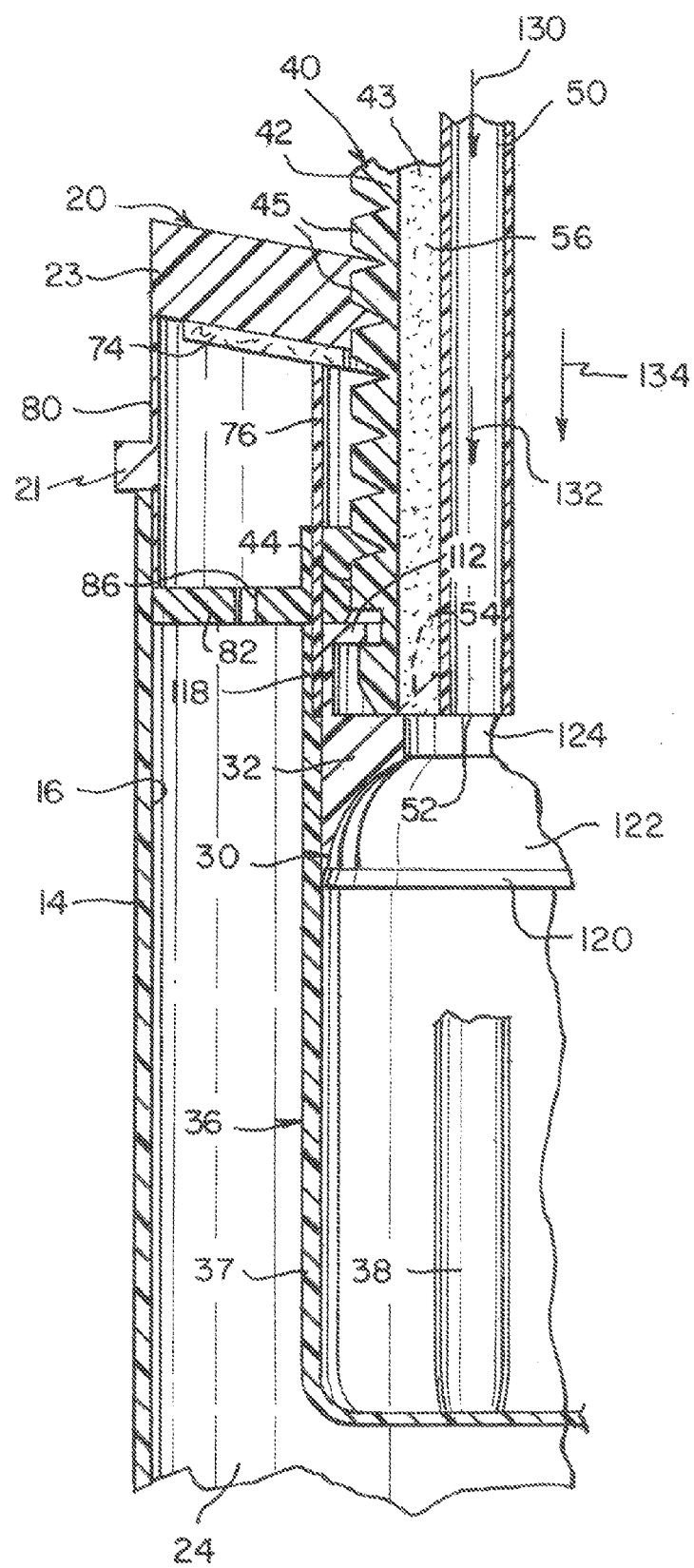
FIG. 4 is a view of the drainage system of FIG. 2 with more components removed for clarity.

As illustrated in enlarged detail in FIGS. 2-4, system 10 further includes a valve 30 with a valve seat 32 and a valve closure member 34, such as a buoyant spherical float, to define a usable volume within the chamber 16. Valve 30 preferably includes an elongated containment cage 36 to control alignment of closure member 34 relative to valve seat 32 over a range of desired containment volumes.

Assembly 12 further includes a movable adjustment member 40 with a shaft 42 passing through the opening 22 in the barrier 20 and terminating within the chamber 16 at a first, interior end 44. The first end 44 of the shaft 42 is connected to the valve seat 32, and the shaft has a plurality of features, such as helical thread 45 along at least a portion of its length engagable with corresponding engagement features, such as mating or matching lands and grooves of a similar helical thread, in a fixed relationship with the barrier 20 to enable the shaft 42 to be advanced into the chamber to reduce the usable volume to be less than the first volume, as described in more detail below.

System 10 includes drain line tubing 50 having a distal end (not shown) coupled to a medical device, such as a shunt or other type of catheter, in fluid communication with the bodily fluid to be drained. A proximal end 52, FIG. 4, of the tubing 50 passes through a central passage 43 in shaft 42 and is in fluid communication with the chamber 16. In one construction, proximal end 52 of tubing 50 is attached directly to valve seat 32 as indicated by dashed line 54; in another construction, a portion of tubing 50 is "potted" within passage 43 of shaft 42 by an epoxy 56 or other polymeric material. The technique of attaching tubing 50 to assembly 12 is a matter of design choice, with engineering factors including the amount of rotation of shaft 52 as described in more detail below.

As illustrated in FIG. 1, this construction of system 10 further includes a secondary drain valve 62 connected to outlet passage 26 by tubing 60. Valve 62 includes a movable control lever 63 which alters fluid flow into secondary bag 64 to a sampling port 65. Also shown in FIG. 1 are lines 66 and 68 in tubing 50 representing the boundaries of a quantity 69 of cerebrospinal fluid being drained into assembly 12. A grip 46, such as a knob, is attached to exterior end region 48 of shaft 42 to enable a user to impart rotation to shaft 42 as described in more detail below.

Additional features in this construction are shown in FIGS. 2-4. Barrier 20 may include vent channels 70 and 72, shown in phantom, defined by cover 23. Preferably, a disk-like filter 74 cooperates with an elastic, cylindrical sleeve 76 to isolate chamber 16 from microbes and other contaminants in the external environment while enabling venting of gases displaced by fluid entering chamber 16. Barrier 20 further includes cylindrical side wall 80 and floor 82 defining vent openings 84 and 86. Rib 21 includes at least one exterior passage 88 through which a retaining element or a securing element may be placed.

External markings 100, 102, 104 and 106 can denote volumes such as 10 ml, 20 ml, 30 ml and 40 ml. Dashed lines 108 and 110 represent minimum and maximum volumes, respectively, which are achieved by moving valve seat 32 via shaft 42. Preferably, assembly 12 is constructed of polymeric materials. In some constructions, at least housing 14 is formed of a translucent material, preferably substantially transparent, to enable visualization of collected fluid within chamber 16.

In the preferred construction illustrated in FIGS. 2-4, valve seat 32 is connected to shaft 42 by fingers or inner projections 112, 114 which slidably engage a channel 116 defined in end 44 of shaft 42. In one construction, fingers 112, 114 extend inwardly from wall 118 of valve seat 32. This connection decouples or isolates seat 32 from the rotation of shaft 42. Valve seat 32 includes chamfer 120, hemispherical sealing region 122 which mates with ball float 34, and inner opening 124 which enables tubing 50 to communicate with chamber 16. In some other constructions, valve seat 32 is formed on, and is a part of, the inner end 44 of shaft 42 and/or the proximal end 52 of tubing 50.

Cage 36 includes elongated guide elements 37, 38, 39 and an additional guide element that is not shown. The plurality of guide elements of cage 36 ensure that ball float 34 will positively engage seat 32 in whatever axial position seat 32 is placed by movement of shaft 42.

Arrows 130 and 132 represent the flow of cerebrospinal fluid or other bodily fluid through tubing 50 into chamber 16, as limited by valve 30. Arrow 134 represents the axial movement of shaft 42 as it is advanced via rotation imparted by a user to reduce the usable volume within chamber 16 from the maximum volume 110 down to a selected volume as small as minimum volume 108.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A system suitable for draining at least one type of bodily fluid from a patient, comprising:
    a chamber capable of being adjusted to hold one of at least a first volume of fluid and a second, smaller volume of fluid, the chamber having an inlet end with a barrier defining an opening and having an outlet end defining an outlet passage;
    a valve including a valve seat and a valve closure member to define a usable volume; and
    a movable adjustment member having a shaft passable through the opening in the barrier and terminating within the chamber at a first end, the first end being connected to the valve seat, the shaft having a plurality of features along at least a portion of its length engagable with corresponding engagement features being in a fixed relationship with the barrier to enable the shaft to be advanced into the chamber to reduce the usable volume to be less than the first volume.

2. The system of claim 1 wherein the valve closure member includes a feature which is buoyant relative to the fluid to be drained.

3. The system of claim 2 wherein the valve includes a cage structure to control movement of the buoyant feature between at least first and second positions representing the first volume and the second volume, respectively.

4. The system of claim 1 wherein the shaft is rotatable and defines a helical thread along at least a portion of its length.

5. The system of claim 4 wherein the adjustment member includes a grip member attached to the shaft, the grip member being graspable by a user of the system to impart rotation to the shaft.

6. The system of claim 1 further including tubing defining a lumen in fluid communication with the valve seat.

7. The system of claim 6 wherein the shaft defines a longitudinal channel and a portion of the tubing passes through the channel.

8. The system of claim 1 further including a sleeve surrounding at least a portion of the shaft to assist in isolating the shaft from fluid within the chamber.

9. The system of claim 1 wherein the barrier includes a filter to restrict entry of microbes past the barrier and into the chamber.

10. A system suitable for draining at least cerebrospinal fluid from a patient, comprising:
    a chamber capable of being adjusted to hold at least a first, maximum volume of fluid and a second, minimum volume of fluid, the chamber having an inlet end with a barrier defining an opening and having an outlet end defining an outlet passage;
    a valve including a valve seat, a buoyant valve closure member to define a usable volume, and a cage structure to control movement of the valve closure member between a first position representing the maximum volume and a second position representing the minimum volume; and
    a mechanically movable adjustment member having a shaft passable through the opening in the barrier and terminating within the chamber at a first end, the first end being connected to the valve seat, the shaft having a helical thread along at least a portion of its length engagable with a corresponding thread defined by the barrier to enable the shaft to be rotatably advanced into the chamber to reduce the usable volume to be less than the maximum volume.

11. The system of claim 10 wherein the adjustment member includes a grip member attached to the shaft, the grip member being graspable by a user of the system to impart rotation to the shaft.

12. The system of claim 10 further including tubing defining a lumen in fluid communication with the valve seat.

13. The system of claim 12 wherein the shaft defines a longitudinal channel and a portion of the tubing passes through the channel.

14. The system of claim 13 further including a sleeve surrounding at least a portion of the shaft to assist in isolating the shaft from fluid within the chamber, and the barrier includes a filter to restrict entry of microbes past the barrier, and an end of the sleeve abuts the filter.

15. A method of adjusting drainage of at least one type of bodily fluid from a patient, comprising:
    selecting an assembly having a chamber capable of holding one of at least a first volume of fluid and a second, smaller volume of fluid, the chamber having an inlet end with a barrier defining an opening and having an outlet end defining an outlet passage, the assembly further including a valve with a valve seat and a valve closure member to define a usable volume, and a movable adjustment member having a shaft passable through the opening in the barrier and terminating within the chamber at a first end, the first end of the shaft being connected to the valve seat, the shaft having a plurality of features along at least a portion of its length engagable with corresponding engagement features being in a fixed relationship with the barrier to enable the shaft to be advanced into the chamber to reduce the usable volume to be less than the first volume;
    coupling a distal end of a tubing to a medical device in fluid communication with the bodily fluid to be drained, a proximal end of the tubing being in fluid communication with the chamber; and
    moving the shaft to adjust the usable volume within the chamber.

16. The method of claim 15 wherein the valve closure member includes a feature which is buoyant relative to the fluid to be drained.

17. The method of claim 16 wherein the valve includes a cage structure to control movement of the buoyant feature between at least first and second positions representing the first volume and the second volume, respectively.

18. The method of claim 17 wherein the shaft is rotatable and defines a helical thread along at least a portion of its length, the adjustment member includes a grip member attached to the shaft, and moving the shaft includes grasping the grip member to impart rotation to the shaft.

19. The method of claim 15 wherein the shaft defines a longitudinal channel and a portion of the tubing passes through the channel.

20. The method of claim 19 further including a sleeve surrounding at least a portion of the shaft to assist in isolating the shaft from fluid within the chamber, and the barrier includes a filter to restrict entry of microbes past the barrier, and an end of the sleeve abuts the filter.

* * * * *